United States Patent
Dubovoy et al.

(10) Patent No.: US 10,406,085 B2
(45) Date of Patent: Sep. 10, 2019

(54) ANTIPERSPIRANT COMPOSITION

(71) Applicant: Colgate-Palmolive Company, New York, NY (US)

(72) Inventors: Viktor Dubovoy, Cresskill, NJ (US); Sandra Wadeer, Flanders, NJ (US); Long Pan, Cherry Hill, NJ (US); Christine Boyke, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/037,383

(22) PCT Filed: Nov. 18, 2013

(86) PCT No.: PCT/US2013/070583
§ 371 (c)(1),
(2) Date: May 18, 2016

(87) PCT Pub. No.: WO2015/073045
PCT Pub. Date: May 21, 2015

(65) Prior Publication Data
US 2016/0279040 A1    Sep. 29, 2016

(51) Int. Cl.
*A61K 8/26* (2006.01)
*A61Q 15/00* (2006.01)
*A61K 8/44* (2006.01)

(52) U.S. Cl.
CPC ............. *A61K 8/26* (2013.01); *A61K 8/44* (2013.01); *A61Q 15/00* (2013.01); *A61K 2800/30* (2013.01); *A61K 2800/51* (2013.01); *A61K 2800/52* (2013.01); *A61K 2800/524* (2013.01); *A61K 2800/874* (2013.01)

(58) Field of Classification Search
CPC ........ A61K 8/26; A61K 8/44; A61K 2800/51; A61K 2800/52; A61Q 15/00
See application file for complete search history.

(56) References Cited

U.S. PATENT DOCUMENTS

| | | | |
|---|---|---|---|
| 2,774,079 A | 9/1988 | Shin et al. | |
| 5,609,855 A | 11/1997 | Oh et al. | |
| 6,403,071 B1 | 6/2002 | Scavone et al. | |
| 6,511,657 B2 | 1/2003 | Avendano et al. | |
| 6,835,373 B2 | 12/2004 | Kolodzik et al. | |
| 8,257,689 B2 * | 9/2012 | Pan ........................ | A61K 8/19 424/66 |
| 2004/0241123 A1 | 12/2004 | Popoff et al. | |
| 2007/0116656 A1 * | 5/2007 | Kux ...................... | A61K 8/044 424/68 |
| 2008/0014160 A1 * | 1/2008 | Faivre ................... | A61K 8/042 424/65 |

FOREIGN PATENT DOCUMENTS

| | | |
|---|---|---|
| DE | 102007035741 | 2/2009 |
| EP | 0269565 | 6/1988 |
| EP | 1787629 | 5/2007 |
| EP | 2 269 565 | 1/2011 |
| FR | 2483230 | 12/1981 |
| WO | WO 03/013452 | 2/2003 |
| WO | WO 08/049650 | 5/2008 |
| WO | WO 09/076591 | 6/2009 |

OTHER PUBLICATIONS

Fitzgerald, 1988, "Chemistry of Basic Commercial Aluminum Hydrolysis Complexes," Ch. 6 in: Alergia, Sociedad Mexicana de Alergia e Immunologia 7:119-292.
International Search Report and Written Opinion in International Application No. PCT/US2013/070583, dated Jul. 14, 2014.

* cited by examiner

*Primary Examiner* — Jianfeng Song

(57) ABSTRACT

Provided herein is an aqueous composition comprising an active antiperspirant ingredient and disodium EDTA, wherein the active antiperspirant ingredient is present in an amount of 0.2 weight % to 3 weight % by total weight of the composition on an anhydrous basis, wherein the active antiperspirant ingredient comprises an aluminum salt, and wherein the pH of the composition is from 2 to 5. The composition may be used as an antiperspirant when applied to the axillary area of a person.

11 Claims, No Drawings

ANTIPERSPIRANT COMPOSITION

BACKGROUND

Antiperspirant compositions are generally applied to an axillary region to limit perspiration and/or to limit or kill bacteria in this region. In this way, body odor caused by bacterial growth is limited or at least reduced.

Antiperspirants can be delivered topically in liquid form including by roll-on or, as an aerosol. When these compositions are applied to the axillary region, solvent evaporates to leave an active antiperspirant ingredient on the skin.

Active antiperspirant ingredients are well known in the art and often comprise an aluminum-containing salt.

Aluminum containing antiperspirant actives (for example, aluminum chlorohydrex and aluminum zirconium glycine salts) are known to contain a variety of polymeric and oligomeric species. It has been clinically shown that in general, the smaller the species, the higher the efficacy for reducing perspiration.

Size exclusion chromatography ("SEC") is a method frequently used for obtaining information on polymer distribution in antiperspirant salt solutions. With appropriate chromatographic columns, generally five distinctive groups of polymer species can be detected in commercial aluminum and aluminum-zirconium complexes. These appear in a chromatogram as peaks 1, 2, 3, 4 and 5, respectively. Peak 1 contains the larger zirconium species (greater than 60 Angstroms). Peaks 2 and 3 contain the larger aluminum species. Peak 4 contains smaller aluminum species (aluminum oligomers, or small aluminum clusters) and these species have been correlated with enhanced efficacy for both aluminum and aluminum/zirconium salts. Peak 5 contains the smallest and most acidic aluminum species.

Due to the high efficacy of Peak 4 species, aluminum salts comprising a high proportion of Peak 4 species may be used in low amounts in antiperspirant compositions whilst maintaining an acceptable level of antiperspirant efficacy.

Ethylenediaminetetraacetic acid (EDTA) and its sodium salts are widely used in the cosmetic and personal care industry as chelating agents and/or preservation system boosters. In particular, tetrasodium EDTA is found in various antiperspirant roll-on formulations. Its aminopolycarboxylic structure of four acetate arms connected by two central amines allows strong hexadentate coordination to heavy metals. However, since aluminum-containing antiperspirant actives carry a large cationic charge, the strong interaction between EDTA and aluminum-containing antiperspirant actives may lead to an instability of the antiperspirant active within antiperspirant formulations, with a consequent loss in antiperspirant efficacy. As further discussed below, the instability is more pronounced in antiperspirant compositions comprising low levels of aluminum-containing antiperspirant actives.

It would therefore be desirable to stabilize aluminum salts in antiperspirant compositions comprising low levels of aluminum-containing salts, and prevent their instability and consequential loss in antiperspirant efficacy.

BRIEF SUMMARY

The present inventors have found that when tetrasodium EDTA is incorporated into compositions comprising low levels of aluminum-containing antiperspirant actives (e.g. less than 6 weight %, on an anhydrous basis), the aluminum-containing actives become unstable and aggregate, and there is an undesirable shift from the active Peak 4 species to the less active Peak 3 species. The present inventors have unexpectedly found that when disodium EDTA is substituted for tetrasodium EDTA, the reduction in stability of the aluminum-containing salt, and the shift from the active Peak 4 species to the less active Peak 3 species is inhibited.

Accordingly, in a first aspect, provided is an aqueous composition comprising an active antiperspirant ingredient and disodium EDTA (ethylenediaminetetraacetate), wherein the active antiperspirant ingredient comprises an aluminum-containing salt, wherein the active antiperspirant ingredient is present in an amount of 0.2 weight % to 3 weight % by total weight of the composition on an anhydrous basis, and wherein the pH of the composition is from 2 to 5.

Preferably, the active antiperspirant ingredient is present in an amount of 0.2 weight % to 2 weight % by total weight of the composition on an anhydrous basis, and more preferably, the active antiperspirant ingredient is present in an amount of 0.5 weight % to 1 weight % by total weight of the composition on an anhydrous basis.

Typically, the composition exhibits a SEC chromatogram having a SEC Peak 4 area: Peak 3 area ratio of at least 1.5. Optionally, the composition exhibits a SEC chromatogram having a Peak 3 and/or Peak 5 area of less than 40% of a total area of Peaks 1, 2, 3, 4 and 5. Further optionally, the SEC chromatogram has no Peak 3 and/or Peak 5 area.

Typically, the pH of the composition is from 2.5 to 4.5, and preferably, from 3 to 4.

Preferably, the active antiperspirant ingredient comprises an ingredient selected from aluminum chlorohydrate, aluminum chloride, aluminum chlorohydrex polyethylene glycol, aluminum chlorohydrex propylene glycol, aluminum dichlorohydrate, aluminum dichlorohydrex polyethylene glycol, aluminum dichlorohydrex propylene glycol, aluminum sesquichlorohydrate, aluminum, sesquichlorohydrate polyethylene glycol, aluminum sesquichlorohydrate propylene, aluminum-zirconium octachlorohydrate, aluminum-zirconium octachlorohydrex gly, aluminum-zirconium pentachlorohydrate, aluminum-zirconium pentachlorohydrex gly, aluminum-zirconium glycol tetrachlorohydrate, aluminum-zirconium tetrachlorohydrex gly, aluminum-zirconium trichlorohydrate, aluminum-zirconium trichlorohydrex gly. More preferably, the active antiperspirant ingredient comprises aluminum chlorohydrate.

Preferably, the disodium EDTA is present in the composition in an amount of 0.1 weight % to 0.4 weight % by total weight of the composition. More preferably, the disodium EDTA is present in the composition in an amount of 0.2 weight % to 0.3 weight % by total weight of the composition.

Optionally, the composition is free of glycine other than glycine complexed with the active antiperspirant ingredient. Further optionally, the composition is free of calcium salts. Still further optionally, the composition is free of tetrasodium EDTA.

Optionally, the composition comprises one or more ingredients selected from: a deodorant active, an emollient, a surfactant, a gelling agent, a fragrance and an emulsifier.

In a second aspect, the present invention provides an aqueous composition comprising an active antiperspirant ingredient and disodium EDTA, wherein the active antiperspirant ingredient comprises an aluminum-containing salt, wherein the aluminum content of the composition is from 0.05 weight % to 1 weight % by total weight of the composition, and wherein the pH of the composition is from 2 to 5.

Preferably, the aluminum content of the composition is from 0.1 weight % to 0.6 weight % by total weight of the composition.

Optionally, the composition is as defined herein.

In a third aspect, the present invention provides a use of disodium EDTA as a preservative in an antiperspirant composition comprising an antiperspirant ingredient for reducing the instability of the antiperspirant ingredient, wherein the antiperspirant ingredient comprises an aluminum-containing salt, and wherein the instability occurs in the presence of an EDTA preservative. Optionally, the EDTA preservative is tetrasodium EDTA.

Typically, the use comprises inhibiting a reduction in Peak 4 area in an SEC chromatogram and/or inhibiting an increase in Peak 3 area in a SEC chromatogram.

Preferably, the composition is as defined herein.

In a fourth aspect, the present invention provides a use of a composition as defined herein as an antiperspirant.

In a fifth aspect, the present invention provides a method comprising applying a composition as defined herein to the skin of a subject. The skin can be an axillary area.

Preferably, the composition is applied from a roll-on dispenser to the subject.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

In one arrangement, the present invention provides an aqueous composition comprising an active antiperspirant ingredient and disodium EDTA, wherein the active antiperspirant ingredient comprises an aluminum-containing salt, wherein the active antiperspirant ingredient is present in an amount of 0.2 weight % to 3 weight % by total weight of the composition on an anhydrous basis, and wherein the pH of the composition is from 2 to 5.

In another arrangement, the present invention provides an aqueous composition comprising an active antiperspirant ingredient and disodium EDTA,
wherein the active antiperspirant ingredient comprises an aluminum-containing salt,
wherein the aluminum content of the composition is from 0.05 weight % to 1 weight % by total weight of the composition,
and wherein the pH of the composition is from 2 to 5.

Active Antiperspirant Ingredient

The active antiperspirant ingredient may comprise aluminum-containing salts including aluminum-zirconium salts.

Any of the known aluminum containing antiperspirant active materials can be utilized in the composition. Antiperspirant actives include, but are not limited to, aluminum chlorohydrate, aluminum chloride, aluminum chlorohydrex polyethylene glycol, aluminum chlorohydrex propylene glycol, aluminum dichlorohydrate, aluminum dichlorohydrex polyethylene glycol, aluminum dichlorohydrex propylene glycol, aluminum sesquichlorohydrate, aluminum, sesquichlorohydrate polyethylene glycol, aluminum sesquichlorohydrate propylene glycol, aluminum-zirconium octachlorohydrate, aluminum-zirconium octachlorohydrex gly, aluminum-zirconium pentachlorohydrate, aluminum-zirconium pentachlorohydrex gly, aluminum-zirconium tetrachlorohydrate, aluminum-zirconium tetrachlorohydrex gly, aluminum-zirconium trichlorohydrate, aluminum-zirconium trichlorohydrex gly, and combinations thereof. Generally, any of the Category I active antiperspirant ingredients listed in the Food and Drug Administration's Monograph on Antiperspirant Drug Products for over-the-counter human use (Oct. 10, 1973) can be used (21 CFR 350.10).

In one embodiment, the antiperspirant active is aluminum chlorohydrate. Preferably, the antiperspirant active is as described and obtained in WO 2009075678 and WO 2009076591.

In some embodiments, the compositions of the present invention are free of glycine, other than glycine that is complexed with the active antiperspirant ingredient. The compositions may further be free of calcium salts such as calcium chloride and calcium carbonate. Gel filtration may be used to remove glycine and calcium salts from the composition. Other suitable methods of removing glycine and calcium salts would be known to the skilled person. Removal of calcium and/or glycine enhances the efficacy of the antiperspirant active and allows a smaller amount to be used in the compositions.

The active antiperspirant ingredient can be incorporated into the compositions of the present invention in an amount of 0.2 weight % to 3 weight % (on an anhydrous basis) by total weight of the composition. In some embodiments, the active antiperspirant ingredient is incorporated into the compositions in an amount of 0.2 weight % to 2.5 weight %, 0.2 weight % to 2 weight %, 0.2 weight % to 1.5 weight % or 0.2 weight % to 1 weight % on an anhydrous basis, by total weight of the composition. Optionally, the active antiperspirant ingredient is incorporated into the composition in an amount of 0.5 weight % to 3 weight %, 0.5 weight % to 2.5 weight %, 0.5 weight % to 2 weight %, 0.5 weight % to 1.5 weight % or 0.5 weight % to 1 weight % on an anhydrous basis, by total weight of the composition. In other embodiments, the active antiperspirant ingredient is incorporated into composition in an amount of 1 weight % to 3 weight %, or 1 weight % to 2 weight % on an anhydrous basis, by total weight of the composition. Preferably, the active antiperspirant ingredient is incorporated into composition in an amount of 0.3 weight % to 1 weight %, or from 0.3 weight % to 0.6 weight % on an anhydrous basis, by total weight of the composition.

In one embodiment, the compositions of the present invention exhibit a SEC profile wherein the ratio of the SEC Peak 4 area:Peak 3 area is at least 10, 9, 8, 7, 6, 5, 4, 3, 2.5, 2, or 1.5. In some embodiments, the percentage of SEC Peak 4 area of a total area of Peaks 1, 2, 3, 4, and 5 in the SEC chromatogram is: at least 40%, 50%, at least 60%, at least 70%, at least 80%, at least 90%, or 95 to 100%.

In another embodiment the compositions exhibit a SEC profile wherein the percentage of SEC Peak 3 area of a total area of Peaks 1, 2, 3, 4, and 5 in the SEC chromatogram is: less than 40%, less than 30%, less than 20%, less than 10%, less than 5%, less than 2% or less than 1%. In another such embodiment, the composition has no SEC Peak 3 area.

In another embodiment, the compositions exhibit a SEC profile wherein the percentage of SEC Peak 5 area of a total area of Peaks 1, 2, 3, 4, and 5 in the SEC chromatogram is: less than 30%, less than 20%, less than 10%, less than 5%, or less than 2%, or less than 1%. In another such embodiment, the compositions have no SEC Peak 5 area.

In another embodiment, the compositions exhibit a SEC profile wherein the percentage of SEC Peak 1 area of a total area of Peaks 1, 2, 3, 4 and 5 in the SEC chromatogram is: less than 10%, less than 5%, less than 2% or less than 1%. In another embodiment, the compositions exhibit no SEC Peak 1 area.

In another embodiment the compositions exhibit a SEC profile wherein the percentage of SEC Peak 2 area of a total area of Peaks 1, 2, 3, 4 and 5 in the SEC chromatogram is: less than 10%, less than 5%, less than 2% or less than 1%. In another embodiment, the compositions exhibit no SEC Peak 2 area.

Aluminum Content

In some embodiments, the compositions of the present invention have an aluminum content of 0.05 weight % to 1 weight %, 0.1 weight % to 1 weight % or 0.1 to 0.6 weight % by total weight of the composition. In other embodiments, the compositions have an aluminum content of 0.2 weight % or 0.3 weight % or 0.4 weight % or 0.5 weight % to 1 weight % by total weight of the composition. In other embodiments, the compositions of the present invention comprise aluminum in an amount of 0.2 weight % to 0.6 weight % or 0.3 weight % to 0.6 weight %.

Disodium EDTA

The compositions of the present invention comprise disodium EDTA. Disodium EDTA is available from a variety of commercial sources such as Edeta® BD. Disodium EDTA may be present in the compositions in an amount of 0.1 weight % to 0.4 weight %, by total weight of the composition. In other embodiments, disodium EDTA is present in the compositions in an amount of 0.1 weight % to 0.3 weight % or 0.1 weight % to 0.2 weight %. In other embodiments, disodium EDTA is present in the compositions in an amount of 0.2 weight % to 0.4 weight % or 0.2 weight % to 0.3 weight %.

pH

In some embodiments, the pH of the compositions is from 2 to 5. In other embodiments, the pH is from 2.5 to 4.5, or from 2 to 4, or from 2 to 3.5 or from 2 to 3. In other embodiments, the pH of the compositions is from 3 to 5, or from 3 to 4.5 or from 3 to 4.

A low pH as defined herein is desirable to minimize irritation to the skin. If the pH of the compositions exceeds 5, precipitation of the aluminum-containing salt may occur, thus reducing the antiperspirant efficacy of the compositions. Generally in compositions comprising high levels of aluminum-containing antiperspirant actives, there is a sufficient amount of aluminum to maintain a low pH and prevent precipitation, even in the presence of a basic component such as the chelant tetrasodium EDTA. However, if a basic component such as tetrasodium EDTA is incorporated into the compositions comprising low levels of aluminum-containing antiperspirant actives (e.g. less than about 4 weight % or 3 weight % on an anhydrous basis), then there is an insufficient amount of aluminum-containing active to maintain a low pH, the pH increases, and precipitation of the aluminum-containing active occur with a concomitant shift from active Peak 4 species to less active Peak 3 species. The present inventors have found that when disodium EDTA is substituted for tetrasodium EDTA in the compositions comprising low levels of aluminum-containing salts as defined herein, the pH may be maintained in a desirable range and precipitation of the aluminum salt is prevented. Thus, in some embodiments, the compositions of the present invention are free of tetrasodium EDTA. A pH of less than 2 is undesirable due to a limited solubility of disodium EDTA and undesirable effects on skin.

Other Components

The compositions of the present invention may further comprise one or more ingredients selected from: a deodorant active, an emollient, a surfactant, a gelling agent, a fragrance and an emulsifier. These ingredients, and the amounts in which they may be incorporated into the compositions, would be known to those of ordinary skill in the art. Specific examples are described below.

The compositions may comprise one more deodorant actives or malodor counteracting materials. Any known deodorant active can be used. Examples of deodorant active include, but are not limited to antimicrobial actives, alcohols, 2,4,4'-trichloro-2'-hydroxy diphenyl ether (Triclosan), octoxyglycerin (SENSIVA™ SC 50), benzethonium chloride, polyhexamethylene biguanides, triethylcitrate, 2-amino-2-methyl-1-propanol (AMP), cetyl-trimethylammonium bromide, cetyl pyridinium chloride, bactericides, and bacteriostats.

Malodor counteracting materials include alpha- or beta-unsaturated esters or mixtures of such materials. In certain embodiments, the level of malodor counteracting composition to deliver a perceivable odor control benefit when delivered in an antiperspirant composition is 0.05 to 0.45 weight % by total weight of the composition. The alpha, beta-unsaturated ester malodor counteracting materials are typically incorporated within an oil phase of the composition.

The compositions may further contain one or more emollients. In one embodiment, the amount of emollients is up to 6% by weight of the composition. In another embodiment, the amount is up to 2%. Emollients are known in the art and are used to impart a soothing effect on the skin. Non-volatile emollients are preferable in the composition. Classes of non-volatile emollients include non-silicone and silicone emollients. Non-volatile, non-silicone emollients include $C_{12-15}$ alkyl benzoate. The non-volatile silicone material can be a polyethersiloxane, polyalkyarylsiloxane or polyethersiloxane copolymer. An illustrative non-volatile silicone material in the composition is phenyl trimethicone. Non-limiting examples of emollients can be found in U.S. Pat. No. 6,007,799. Examples include, but are not limited to, PPG-14 butyl ether, PPG-15 stearyl ether, PPG-3 myristyl ether, stearyl alcohol, stearic acid, glyceryl monoricinoleate, isobutyl palmitate, glyceryl monostearate, isocetyl stearate, sulphated tallow, oleyl alcohol, propylene glycol, isopropyl laurate, mink oil, sorbitan stearate, cetyl alcohol, hydrogenated castor oil, stearyl stearate, hydrogenated soy glycerides, isopropyl isostearate, hexyl laurate, dimethyl brassylate, decyl oleate, diisopropyl adipate, n-dibutyl sebacate, diisopropyl sebacate, 2-ethyl hexyl palmitate, isononyl isononanoate, isodecyl isononanoate, isotridecyl isononanoate, 2-ethyl hexyl palmitate, 2-ethyl hexyl stearate. Di-(2-ethyl hexyl) adipate), Di-(2-ethyl hexyl) succinate, isopropyl myristate, isopropyl palmitate, isopropyl stearate, octacosanol, butyl stearate, glyceryl monostearate, polyethylene glycols, oleic acid, triethylene glycol, lanolin, castor oil, acetylated lanolin alcohols, acetylated lanolin, petrolatum, isopropyl ester of lanolin, fatty acids, mineral oils, butyl myristate, isostearic acid, palmitic acid, PEG-23 oleyl ether, olelyl oleate, isopropyl linoleate, cetyl lactate, lauryl lactate, myristyl lactate, quaternised hydroxy alkyl, aminogluconate, vegetable oils, isodecyl oleate, isostearyl neopentanoate, myristyl myristate, oleyl ethoxy myristate, diglycol stearate, ethylene glycol monostearate, myristyl stearate, isopropyl lanolate, paraffin waxes, glycyrrhizic acid, hydrocyethyl stearate amide.

In one embodiment, the emollient is selected from linear silicones, cyclic silicones, hydrocarbons, polyhydroxy alcohols having more than 3 carbon atoms, liquid or solid polyalkyleneglycol ethers containing a polypropylene glycol (PPG) moiety and terminating in an alkyl ether, and combinations thereof. In another embodiment, the emollient is a volatile silicone having a flash point of 100° C. or less, such as cyclomethicone, cyclopentasiloxane, or trisiloxane. By volatile silicone material, it is meant that the material has a measurable vapor pressure at ambient temperature. In another embodiment, the emollient is a nonvolatile silicone, such as dimethiconol or a longer chain dimethicone.

The compositions of the present invention may further comprise one or more surfactants. The surfactant can be included in any desired amount. In one embodiment, the amount of surfactant is 2 to 12 weight % by total weight of the composition. The amount in the composition is based on the as supplied material. In another embodiment, the amount of surfactant is 3 to 10 weight % by weight. In one embodiment, when the composition is an oil-in-water roll-on formula, the amount of surfactant is from 2 to 5 weight % by total weight of the composition. Examples of the surfactant include, but are not limited to, nonionic surfactants, silicone surfactants, and combinations thereof.

Nonionic surfactants that can be used include, but are not limited to, (a) sorbitan esters and ethoxylated sorbitan esters (for example PEG-20 sorbitan isostearate, sorbitan monolaurate, polysorbate-20, polysorbate-40, polysorbate-60, polysorbate-80); (b) ethoxylates (for example, Ceteth-20, PEG-30 castor oil. PEG-40 hydrogenated castor oil, PEG-60 hydrogenated castor oil. Laureth-7, Isolaureth-6, Steareth-10. Steareth-20. Steareth-21, Steareth-100. Ceteareth-12, Oleth-5, Oleth-10); (c) ethoxylated adducts (for example, PEG-25 stearate, glyceryl stearate and PEG-100 stearate): (d) PEG esters (for example, PEG-8 oleate, PEG-8 laurate, PEG-8 dilaurate. PEG-12 dilaurate, PEG-80 diisostearate, PEG-40 stearate); (e) propoxylates (for example, PPG-10 butanediol, PPG-50 oleyl ether, PPG-2-ceteareth-9, PPG-3-deceth-3. PPG-5-ceteth-20); (f) ethoxylated modified triglycerides (for example, PEG-20 corn glycerides. PEG-12 palm kernel glycerides); (g) alkylphenol aromatic ethoxylates (for example, dinonylphenol ethoxylate with 9 moles of EO, octylphenol ethoxylate with 20 moles of EO, octylphenol ethoxylate with 40 moles of EO): (h) block copolymers that are alkoxylated glycols having ethoxylated and propoxylated segments (for example, POLOXAMER™ 182 and 234. POLOXAMER™ 105 Benzoate, and MEROXAPOL™ 174); and combinations thereof. In one embodiment, the nonionic surfactant is selected so that it has an HLB (hydrophilic-lipophilic balance) value of 8-16 (more particularly 8-12).

In one embodiment, the nonionic surfactant is selected from ethoxylated nonionic surfactants and propoxylated non-ionic surfactants. Example of these include, but are not limited to, Steareth 2, Steareth 20, and Steareth 21. In an oil in water composition embodiment, a combination of two surfactants, one having an HLB value of 2 to 8 (such as Steareth 2) and the other having an HLB of 9 to 18 (such as Steareth 20 and 21), can be used.

Examples of silicone surfactants can be found in U.S. Pat. No. 6,485,716, which is incorporated herein by reference only for the listing of the silicone surfactants. Suitable silicone surfactants include silicone polyglucosides (for example, octyl dimethicone ethoxy glucoside) and silicone copolyols having an HLB (hydrophilic lipophilic balance) value of less than 8. The HLB value may be measured in a variety of ways such as described in conventional references or found listed in tables of data recording such values. It is intended that any type of HLB measurement technique may be used.

In general, silicone copolyols include, but are not limited to, copolyols of the following Formulae I and II. Formula I materials may be represented by: $(R^{10})_3SiO[(R^{11})_2SiO]xSi(R^{12})(R^bO((C_2H_4O))_p(C_3H_6O)_s(R^c)O]_ySi(R^{13})$ wherein each of $R^{10}$, $R^{11}$, $R^{12}$, and $R^{13}$ may be the same or different and each is chosen from C1-C6 alkyl; $R^b$ is the radical $—C_mH2_m—$; $R^c$ is a terminating radical which can be hydrogen, an alkyl group of one to six carbon atoms, an ester group such as acyl, or an aryl group such as phenyl; m has a value of two to eight: p and s have values such that the oxyalkylene segment $—(C_2H_4O)_p—(C_3H_6O)_{·s}—$ has a molecular weight in the range of 200 to 5,000; the segment preferably having fifty to one hundred mole percent of oxyethylene units $—((C_2H_4O)_p—$ and one to fifty mole percent of oxypropylene units $—(C_3H_6O)_{·s}—$; x has a value of 8 to 400; and y has a value of 2 to 40. Preferably each of $R^{10}$, $R^{11}$, $R^{12}$, and $R^{13}$ is a methyl group; $R^c$ is H; m is preferably three or four whereby the group $R^b$ is most preferably the radical $—(CH_2)_3—$; and the values of p and s are such as to provide a molecular weight of the oxyalkylene segment $—(C_2H_4O)_p—(C_3H_6O)_s—$ of between 1,000 to 3.000. In one embodiment, p and s should each have a value of 18 to 28. In one embodiment, the silicone copolyol is dimethicone copolyol.

A second siloxane polyether (copolyol) has the Formula II: $(R^{10})_3SiO[(R^{11})_2SiO]xSi(R^{12})(R^bO(C_2H_4O)_pR^c)O]ySi(R^{13})_3$ wherein p has a value of 6 to 16; x has a value of 6 to 100; and y has a value of 1 to 20 and the other moieties have the same definition as defined in Formula I.

It should be understood that in both Formulas I and II shown above, that the siloxane-oxyalkylene copolymers may, in alternate embodiments, take the form of end-blocked polyethers in which the linking group $R^b$, the oxyalkylene segments, and the terminating radical R occupy positions bonded to the ends of the siloxane chain, rather than being bonded to a silicon atom in the siloxane chain. Thus, one or more of the $R^{10}$, $R^{11}$, $R^{12}$, and $R^{13}$ substituents that are attached to the two terminal silicon atoms at the end of the siloxane chain can be substituted with the segment $—R^b—O—(C_2H_4O)_p—(C_3H_6O)_s—R^c$ or with the segment $—R^b—O—(C_2H_4O)—R^c$. In some instances, it may be desirable to provide the segment $—R^b—O—(C_2H_4O)_p—(C_3H_6O)_s—R^c$ or the segment $—R^b—O—(C_2H_4O)_p—R^c$ at locations which are in the siloxane chain as well as at locations at one or both of the siloxane chain ends.

Particular examples of suitable dimethicone copolyols are available either commercially or experimentally from a variety of suppliers including Dow Corning Corporation, Midland, Mich.; General Electric Company, Waterford, N.Y.; Witco Corp., Greenwich, Conn.; and Goldschmidt Chemical Corporation, Hopewell. Va. Examples of specific products include DOW CORNING 5225C from Dow Corning, which is a 10% dimethicone copolyol in cyclomethicone; DOW CORNING 2-5185C, which is a 45-49% dimethicone copolyol in cyclomethicone; SILWET L-7622 from Witco; ABIL3 EM97 from Goldschmidt, which is an 85% dimethicone copolyol in D5 cyclomethicone; and various dimethicone copolyols available either commercially or in the literature.

It should also be noted that various concentrations of the dimethicone copolyols in cyclomethicone can be used. While a concentration of 10% in cyclomethicone is frequently seen commercially, other concentrations can be made by stripping off the cyclomethicone or adding additional cyclomethicone. The higher concentration materials such as DOW CORNING 2-5185 can be used in one embodiment. In a preferred embodiment, 0.5 to 5 wt. % (particularly 1 to 2 wt. %) of a 10% silicone copolyol such as dimethicone copolyol in cyclomethicone mixture may be used.

Gelling agents may further be incorporated into the compositions. Examples of gelling agents include, but are not limited to, waxes, esters of fatty acid and fatty alcohol, triglycerides, partially or fully hydrogenated soybean oil, partially or fully hydrogenated castor oil, other partial or fully hydrogenated plant oils, stearyl alcohol, or other cosmetically acceptable materials, which are solid or semi-solid at room temperature and provide a consistency suitable for application to the skin.

In one embodiment, the gelling agent comprises a combination of hydrogenated soybean oil and a hydrocarbon of the formula $C_nH_{2n+2}$, wherein n is 20 to 100, and the hydrocarbon is at least 90% linear. In this embodiment, the antiperspirant composition has a structure that provides a better delivery of the antiperspirant to the skin.

In certain embodiments, the fully or partially hydrogenated soybean oils are those described in US2008/0187504A1 and US2008/0187503A1. The hydrogenated soybean oil from US2008/0187504A1 is almost, but not fully hydrogenated. The amount of hydrogenation is measured by the iodine value. The iodine value can be measured by ASTM D5554-95 (2006). The iodine value of the hydrogenated soybean oil used herein is greater than 0 to 20. In one embodiment, the iodine value is 1 to 5. The partially hydrogenated soybean oil from US2008/0187503A1 has a melting point that of −15° C. (5' F) to 38° C. (100° F.). In another embodiment, the melting point is 26° C. (80° F.) to 38° C. (100° F.). To obtain the desired melting point, the oil can be partially hydrogenated or a blend of non-hydrogenated with partially or fully hydrogenated oils and/or waxes.

The partially or fully hydrogenated soybean oil is present in an amount up to 20% by weight of the composition. In another embodiment, the amount is up to 10% by weight. In one embodiment, the amount is at least 1, 2, 3, 4, 5, 6, 7, 8, or 9% by weight. In another embodiment, the amount is less than 10, 9, 8, 7, 6, 5, 4, 3, 2, 1% by weight. Any of the preceding minimum and maximum amounts can be combined to form any range of values.

The hydrocarbon is a hydrocarbon of the formula $C_nH_{2n+2}$, wherein n is 20-100, and the hydrocarbon is at least 90% linear. In one embodiment, the hydrocarbon is a paraffin. In another embodiment, the hydrocarbon is polyethylene/polymethylene. An example of a polyethylene can be found in U.S. Pat. No. 6,503,491. In another embodiment, the polyethylene has a weight average molecular weight of 300 to 3000 and a melting point of 50 to 129° C.

When water is present, for example in a liquid roll-on composition, the amount of water in the composition is the amount to make a 100% by weight composition after all of the materials, including any optional materials, are added to the composition. In certain embodiments, the amount of water is at least 20%, 30%, 40%, 50%, 60%, 70%, 80%, or 85% by weight of the composition.

The total amount of solids in the composition is the amount of non-volatile materials in the composition. The percentage of solids is measured by a CEM Smart System moisture/solids analyzer which uses microwave energy to dry the samples. In one embodiment, the total amount of solids is less than 25%. In another embodiment, the total amount of solids is less than 20%.

The compositions of the present invention may also contain particulates which include but are not limited to talc, mica, fragrance encapsulates, or hydrophobically modified starches, such as aluminum starch octenyl succinate (MACKADERM™ ASTRO-DRY™ from McIntyre Group Ltd.). If the composition is in a liquid form and dispensed through a roll-on applicator, the average particle size of the suspended material is such that the particles can pass through the application to prevent the ball applicator from malfunctioning. Usually, the average particle size does not exceed 150 microns.

Additional components of the antiperspirant compositions optionally include any components suitable for use in such compositions which are known in the art. Such components include additional preservative agents such as quaternary ammonium compounds (for example, 2-amino-2-methyl-1-propanol (AMP), cetyl-trimethylammonium bromide, cetyl pyridinium chloride, 2, 4, 5 N-trichloro-2N-hyroxydiphenylether (Triclosan) and various zinc salts), colorants, emulsifiers etc. In some embodiments, the compositions of the present invention are free of preservatives other than disodium EDTA. Antioxidants may also be incorporated into the composition, preferably to act as ingredient protectants and for maintenance of long-term stability of the composition. Suitable antioxidants include Tinogard, manufactured by Ciba Specialty Chemicals, Basel, Switzerland.

Methods of Use

The compositions may be used to formulate antiperspirants having improved efficacy. Accordingly, provided is use of the compositions as defined herein as an antiperspirant. The antiperspirant may be in the form of a solid such as a stick or cream, or in the form of a gel, liquid, or aerosol. The form of the composition and the antiperspirant product may be a suspension or emulsion. In a preferred embodiment, the composition is a liquid suitable for application through a roll-on dispenser.

Further provided is an antiperspirant composition dispenser comprising a composition as described herein in a suitable container capable of dispensing the composition topically. Such containers are known in the art and include roll-on dispensers and pressurized aerosol containers.

Still further provided is a method comprising applying a composition as described herein to the skin (preferably an axillary area) of a subject.

The compositions may be manufactured using methods known in the art. Typically, the ingredients are combined and optionally heated where components need to be melted. Desirably, volatile materials such as fragrant materials are incorporated in the composition in the latter stages of a mixing cycle in order to avoid volatilisation thereof. After mixing the ingredients, the composition may be poured directly into the dispensers and the container capped to preserve the product until use.

Use of Disodium EDTA

In another arrangement, the present invention provides a use of disodium EDTA as a preservative or chelant in an antiperspirant composition comprising an antiperspirant ingredient for reducing the instability of the antiperspirant ingredient which occurs in the presence of an EDTA preservative, wherein the antiperspirant ingredient comprises an aluminum-containing salt. In a further arrangement, the present invention provides a method of reducing the instability of an antiperspirant ingredient in a composition which occurs in the presence of an EDTA preservative, wherein the method comprises incorporating disodium EDTA into the composition, and wherein the antiperspirant ingredient comprises an aluminum-containing salt. The composition may be as defined herein. The EDTA preservative may be tetrasodium EDTA.

The term "instability" refers to an aggregation and/or precipitation of the aluminum-containing salt. Further, with reference to an SEC chromatogram, the term may additionally refer to a shift from active Peak 4 species to less active Peak 3 species.

Thus, in one embodiment, the use or method comprises inhibiting a reduction in Peak 4 area in an SEC chromatogram and/or inhibiting an increase in Peak 3 area in a SEC chromatogram. Accordingly, the use or method may comprise inhibiting a decrease in the ratio of the Peak 4 area:Peak 3 area. In another embodiment, the use or method comprises inhibiting precipitation/aggregation of the aluminum-containing salt. In some embodiments, the use or method comprises inhibiting a decrease in the ratio of the Peak 4 area:Peak 3 area and inhibiting precipitation/aggregation of the aluminum salt.

Various ingredients may promote instability of aluminum-containing salts. In particular, the present inventors have found that when tetrasodium EDTA is incorporated into compositions with low levels of an aluminum-containing antiperspirant active, precipitation/aggregation of the aluminum salt may occur, and additionally, there may be a shift from active Peak 4 species to less active Peak 3 species. However, when disodium EDTA is substituted for tetrasodium EDTA in accordance with the present invention, the instability of the aluminum salt (i.e. precipitation/aggregation and/or the shift from active Peak 4 species to Peak 3 species) is reduced.

The invention is further illustrated in the following non-limiting Examples.

Size Exclusion Chromatography (SEC): The polymerization of the antiperspirant actives in aqueous solutions and the correspondent gelation process are followed by monitoring the molecular weight profile of the polyoxohalides in time by SEC. The relative retention time ("Kd") for each of these peaks varies depending on the experimental conditions, but the peaks remain relative to each other. Data for SEC is obtained using an SEC chromatogram using the following parameters: Waters®600 analytical pump and controller, Rheodyne® 7725I injector, Protein-Pak® 125 (Waters) column, Waters 2414 Refractive Index Detector, 5.56 mM nitric acid mobile phase, 0.50 ml/min flow rate, 2.0 microliter injection volume. Data is analyzed using Water® Empower software (Waters Corporation, Milford, Mass.). The concentration of the antiperspirant in solution does not affect the retention time in the machine.

Example 1—Liquid Roll-on Formulations

Table 1 illustrates roll-on antiperspirant formulations.

TABLE 1

| Ingredient | Roll-on antiperspirant formulations | | | | | | | | |
| --- | --- | --- | --- | --- | --- | --- | --- | --- | --- |
| | 1 | 2 | 3 | 4 | 5 | 6 | 7 | 8 | 9 |
| Steareth-20 | 0.6 | 0.6 | 0.6 | 0.6 | 0.6 | 0.6 | 0.6 | 0.6 | 0.6 |
| Steareth-21 | 0.6 | 0.6 | 0.6 | 0.6 | 0.6 | 0.6 | 0.6 | 0.6 | 0.6 |
| Steareth-2 | 2.3 | 2.3 | 2.3 | 2.3 | 2.3 | 2.3 | 2.3 | 2.3 | 2.3 |
| PPG-15 stearyl ether | 1.56 | 1.56 | 1.6 | 1.6 | 1.56 | 1.56 | 1.56 | 1.56 | 1.0 |
| Cyclopentasiloxane | 0 | 0 | 1.5 | 0 | 0 | 0 | 0 | 0 | 0 |
| PPG-3 myristyl ether | 0 | 0 | 0 | 0 | 0 | 0 | 0 | 0 | 0.6 |
| Aluminum starch octenyl succinate (ASTODRY ™) | 0 | 0 | 0 | 0 | 0 | 1.5 | 1 | 0 | 0 |
| Jojoba oil | 0 | 0 | 3.5 | 0 | 0 | 0 | 0 | 0 | 0 |
| Soybean oil S100 (Cargill) | 3 | 1.5 | 0 | 3 | 1.5 | 0 | 0 | 0 | 1.5 |
| Soybean oil S500 (Cargill) | 0 | 0 | 0 | 0 | 0 | 1 | 1 | 3 | 0 |
| Hydrogenated polyisobutene (FANCOL ™ Polyiso-200) | 0 | 0 | 0 | 0 | 0 | 0 | 0 | 0 | 1.5 |
| Isodecane (Permethyl 99A) | 1.5 | 0 | 0 | 0 | 0 | 0 | 0 | 0 | 0 |
| Diisopropyl Adipate (Ceraphyl 230) | 0 | 1.5 | 0 | 0 | 0 | 0 | 0 | 0 | 0 |
| Neopentyl glycol diheptonoate and isododecane (LEXFEEL ™ D5) | 0 | 0 | 0 | 0 | 1.5 | 0 | 0 | 0 | 0 |
| Aluminum Chlorohydrate (anhydrous) | 2.5 | 2.5 | 2 | 2 | 1.5 | 1.5 | 1 | 1 | 0.5 |
| Water | QS | QS | QS | QS | QS | QS | QS | QS | QS |
| di-tertiary butyl-para-cresol | 0.05 | 0.05 | 0.05 | 0.05 | 0.05 | 0.05 | 0.05 | 0.05 | 0.05 |
| Quaternium 15 | 0.1 | 0.1 | 0.1 | 0.1 | 0.1 | 0.1 | 0.1 | 0.1 | 0.1 |
| Fragrance | 1 | 1 | 1 | 1 | 1 | 1 | 1 | 1 | 1 |
| Disodium EDTA | 0.2 | 0.25 | 0.25 | 0.1 | 0.3 | 0.4 | 0.25 | 0.2 | 0.25 |

Example 2—Effects of Tetrasodium EDTA and Disodium EDTA on the Stability of ACH (1)

Samples were prepared as set out in Table 2. Tetrasodium EDTA and disodium EDTA powder were weighed in a scintillation vial, using a laboratory scale with 0.0001 g accuracy. An automatic pipette was calibrated and used to deliver the specified amounts of ACH solution (purchased from Gulbrandsen) to ensure negligible variation in aluminum concentrations. ACH solution was added to the relevant EDTA powders and subsequently diluted with deionised water to total solution weight of 10 g. Samples were placed in a sonicator for 5 minutes to allow complete dissolution, prior to aging at 50° C. for 5 days. Disodium and tetrasodium EDTA concentrations of 0.2, 0.25, or 0.3 wt. % were tested in solutions comprising ACH in an amount of 0.3 weight % or 1 weight % on an anhydrous basis, by total weight of the composition (This is corresponds to an amount of aluminum of 0.1 weight % and 0.3 weight %, respectively). The pH, appearance and SEC profile of the compositions were determined after aging. The results are provided in Table 2.

active Peak 3 and Peak 2 species, indicating aggregation of the aluminum salt. In contrast, it is observed that the aggregation is significantly reduced in the presence of the same concentrations of disodium EDTA. Similarly, it is observed that when 0.2 weight % tetrasodium EDTA is incorporated into a composition comprising 1 weight % ACH (0.3 weight % aluminum), there is a significant shift from active Peak 4 species to the larger, less active Peak 3 and Peak 2 species, which is not observed in the presence of 0.2 weight % disodium EDTA.

TABLE 2

Sample preparation, pH and appearance
Table 2: Sample Preparation for 0.1% Al (1-7) or 0.3% Al (8-9) ACH with 0.2-0.3% EDTA (di vs. tetrasodium)

| | Theoretical | | | Experimental | | | | |
| --- | --- | --- | --- | --- | --- | --- | --- | --- |
| Label | ACH (g) | % $Na_2$-EDTA | % $Na_4$-EDTA | $Na_2$-EDTA (g) | $Na_4$-EDTA (g) | ACH (g) | Total (g) | pH* | Visual Test |
| 1 | 0.2667 | 0.2 | | 0.0197 | | 0.2735 | 10.0588 | 4.4 | PASS |
| 2 | 0.2667 | 0.25 | | 0.0255 | | 0.2757 | 10.0049 | 4.35 | PASS |
| 3 | 0.2667 | 0.3 | | 0.0303 | | 0.2814 | 10.0161 | 4.4 | PASS |
| 4 | 0.2667 | | 0.2 | | 0.0193 | 0.2757 | 10.0183 | 5.38 | PASS |
| 5 | 0.2667 | | 0.25 | | 0.0250 | 0.2700 | 10.0334 | 5.3 | PASS |
| 6 | 0.2667 | | 0.3 | | 0.0297 | 0.2749 | 10.0286 | 5.3 | FAIL (↓) |
| 7 | 0.8000 | 0.2 | | 0.0201 | | 0.7994 | 10.0138 | 4.12 | PASS |
| 8 | 0.8000 | | 0.2 | | 0.0195 | 0.8011 | 9.9991 | 4.91 | PASS |

*pH was measured after thermal aging

It can be seen from Table 2 that at all concentrations of tetrasodium EDTA tested, the pH of the compositions comprising 0.3 weight % ACH (0.1% aluminum) exceeds pH 5. In contrast, at all concentrations of disodium EDTA tested, the pH of these compositions was maintained below 5. Furthermore, with 0.3 weight % tetrasodium EDTA, there was a visible precipitation of ACH. In contrast, no visible precipitation occurred with disodium EDTA at any of the concentrations tested.

It is observed in a SEC profile of ACH solution that in the absence of EDTA, ACH exhibits strong Peak 4 activity with no Peak 3 or Peak 2 activity. It is observed that in the presence of all concentrations of tetrasodium EDTA tested with 0.3 weight % ACH solution (0.1 weight % aluminum), there is a shift from active Peak 4 species to the larger, less Example 3—Effects of Tetrasodium EDTA and Disodium EDTA on the Stability of ACH (2)

Stock solutions of 0.4 weight %, 1.2 weight %, 2.4 weight % and 4.7 weight % ACH (on an anhydrous basis; corresponding to 0.1 weight %, 0.3 weight %, 0.6 weight % and 1.2 weight % aluminum, respectively) were prepared using ACH powder (purchased from Summit). Subsequently, 10 g of the ACH stock solution was added to 0.025 g of disodium or tetrasodium EDTA powders according to Table 3 and as described in Example 2. Following preparation, the samples were aged at 50° C. for 18 hours. The appearance of the samples was noted before and after aging, and SEC was conducted on the aged samples to determine any changes in Peak 4/Peak 3 areas.

TABLE 3

Sample preparation
Table 3: Stability of 0.1-0.6% Al (ACH103 with Di and Tetrasodium EDTA

| Theoretical | | | | | Experimental | | | | | |
| --- | --- | --- | --- | --- | --- | --- | --- | --- | --- | --- |
| Al (%) | ACH (g) | $Na_2$-EDTA (g) | $Na_4$-EDTA (g) | Total (g) | Al (%) | ACH (g) | $Na_2$-EDTA (g) | $Na_4$-EDTA (g) | Total (g) | pH* |
| 0.10 | 0.0394 | 0.025 | | 10 | 0.10 | 9.9976 | 0.0253 | | 10.0229 | 4.57 |
| 0.10 | 0.0394 | | 0.025 | 10 | 0.10 | 9.9961 | | 0.0250 | 10.0211 | 7.38 |
| 0.30 | 0.1181 | 0.025 | | 10 | 0.30 | 10.0033 | 0.0256 | | 10.0289 | 4.43 |
| 0.30 | 0.1181 | | 0.025 | 10 | 0.30 | 9.9992 | | 0.0248 | 10.0240 | 5.23 |
| 0.60 | 0.2362 | 0.025 | | 10 | 0.60 | 10.0010 | 0.0247 | | 10.0257 | 4.30 |
| 0.60 | 0.2362 | | 0.025 | 10 | 0.60 | 10.0078 | | 0.0250 | 10.0328 | 4.92 |
| 1.20 | 0.4724 | 0.025 | | 10 | 1.20 | 10.0024 | 0.0248 | | 10.0272 | 4.26 |
| 1.20 | 0.4724 | | 0.025 | 10 | 1.20 | 9.9979 | | 0.0246 | 10.0225 | 4.58 |

*pH was measured after thermal aging at 50° C.

It can be seen from Table 3 at all concentrations of ACH tested, tetrasodium EDTA promoted a higher pH than disodium EDTA. In particular, compositions comprising 0.4 weight % ACH and 1.2 weight % ACH had a pH of greater than 5 in the presence of tetrasodium EDTA, but not disodium EDTA.

It is observed that pre-aging, tetrasodium EDTA causes visible precipitation in 0.4 weight %, 1.2 weight %, and 2.4 weight % ACH solutions. In contrast, no visible precipitation occurred in 0.4 weight %, 1.2 weight %, and 2.4 weight % ACH solutions with disodium EDTA. Precipitated aluminum salts are unable to function as antiperspirant actives. Also, tetrasodium EDTA and disodium EDTA on aged samples (0.4 weight % ACH: 1.2 weight % ACH; 2.4 weight % ACH) was tested and observed. Whilst the effects of tetrasodium EDTA on the precipitation of the aluminum-containing salts are less pronounced in the aged samples, disodium EDTA did not induce any precipitation. Thus it may be concluded that aluminum-containing antiperspirant actives are significantly more stable in the presence of disodium EDTA as compared to tetrasodium EDTA.

SEC profiles of ACH solutions aged in the presence of either tetrasodium EDTA or disodium EDTA were prepared. It was observed that at all concentrations of ACH tested (0.4 weight % ACH; 1.2 weight % ACH: 2.4 weight %; ACH: 4 weight % ACH), there was a shift from active Peak 4 species to the larger, less active Peak 3 species, indicating aggregation of the aluminum salt. The ratio of the Peak 4 area:Peak 3 area for each sample is further indicated in Table 4. It can be seen from Table 4 that the ratio of Peak 4 area:Peak 3 area is significantly higher for aged compositions comprising disodium EDTA as compared to tetrasodium EDTA, particularly, at the lower ACH concentrations tested. These data demonstrate that disodium EDTA is capable of reducing the instability of aluminum-containing antiperspirant actives which is seen in the presence of tetrasodium EDTA.

TABLE 4

0.1-1.2% Al (0.4-4 weight %) ACH 103 w/0.25% EDTA

|  | % Al | Peak 3 | Peak 4 | Peak 4/3 |
|---|---|---|---|---|
| $Na_2$ EDTA | 0.1 | 38.85 | 61.15 | 1.57 |
|  | 0.3 | 32.05 | 67.95 | 2.12 |
|  | 0.6 | 35.5 | 64.5 | 1.82 |
|  | 1.2 | 41.54 | 56.91 | 1.37 |
| $Na_4$ EDTA | 0.1 | 0 | 0 | 0.00 |
|  | 0.3 | 75.7 | 24.3 | 0.32 |
|  | 0.6 | 60.74 | 39.26 | 0.65 |
|  | 1.2 | 56.24 | 43.76 | 0.78 |

Example 4—Effects of Tetrasodium EDTA and Disodium EDTA on the Stability of Aluminum Zirconium Tetrachlorohydrex-Glycine (ZAG)

Stock solutions of 0.5 weight %, 1.5 weight %, 3 weight % and 6 weight % ZAG (on an anhydrous basis; corresponding to 0.1 weight %, 0.3 weight %, 0.6 weight % and 1.2 weight % aluminum, respectively) were prepared using ZAG powder (purchased from Summit). Tetrasodium EDTA or disodium EDTA was incorporated into the solutions as described in Example 2. The methods according to Example 2 were repeated using the prepared ZAG solutions, with the exception that the samples were aged for 24 hours.

It was observed that the SEC profile of standard ZAG solutions prior to thermal aging that the SEC profile of ZAG solutions that have been aged in the presence of tetrasodium EDTA or disodium EDTA (0.4 weight % ZAG/0.1 weight % aluminum and 1.2 weight % ZAG/0.3 weight % aluminum) indicate a significantly reduced amount of the less desirable Peak 5 aluminum species in samples with disodium EDTA. The reduction is not as pronounced in compositions comprising 2.4 wt. % ZAG/0.6 weight % aluminum and 4 wt. % ZAG/i weight % aluminum. A larger proportion of aggregated Peak 2 aluminum species was observed in ZAG samples with tetrasodium EDTA as compared to corresponding samples with disodium EDTA, with the most pronounced difference observed at lower ZAG concentrations. It may be concluded from these data that disodium EDTA is effective at reducing the instability of ZAG, which occurs in the presence of tetrasodium EDTA.

Relative SEC peak areas and an estimation of antiperspirant efficacy are reported in Table 5. The approximation of efficacy is the ratio of the sum of the Peak 4 and 5 areas (small aluminum species) over peaks 2 and 3 areas (large aluminum species).

TABLE 5

SEC relative peak areas

|  | Sample | Peak 2 (%) | Peak 3 (%) | Peak 4 (%) | Peak 5 (%) | Efficacy* |
|---|---|---|---|---|---|---|
| $Na_4$ EDTA | 0.1% Al | 17.16 | 25.29 | 55.54 | 2.01 | 3.3 |
|  | 0.3% Al | 4.91 | 11.69 | 61.99 | 21.41 | 25.1 |
|  | 0.6% Al | 4.82 | 10.77 | 58.69 | 25.73 | 29.5 |
|  | 1.2% Al | 3.45 | 21.88 | 46.61 | 28.06 | 29.9 |
| $Na_2$ EDTA | 0.1% Al | 4.19 | 24.50 | 52.86 | 18.45 | 20.3 |
|  | 0.3% Al | 0.00 | 14.82 | 57.70 | 27.48 | 31.4 |
|  | 0.6% Al | 1.83 | 10.43 | 58.87 | 28.87 | 33.7 |
|  | 1.2% Al | 2.48 | 19.48 | 48.44 | 29.61 | 31.8 |

*Efficacy parameter equals (Peak 5 + Peak 4)/(Peak 3 + Peak 2)

It can be seen from Table 5 that the estimated antiperspirant efficacy of ZAG is higher in the presence of disodium EDTA, as compared to tetrasodium EDTA. The difference is most pronounced at the lower concentrations of ZAG tested.

It should be noted that whilst equivalent weight concentrations of disodium and tetrasodium EDTA were tested in the present Examples, since the two compounds are of different molecular weights, different amounts of $EDTA^{4-}$ were delivered. However, given the lower weight proportion of sodium relative to $EDTA^{4-}$ in disodium EDTA as compared to tetrasodium EDTA, the prepared samples containing disodium EDTA powder actually contained 2 to 5% more $EDTA^{4-}$ (on a molar basis) than their tetrasodium counterparts at an equal weight concentration. Thus, any instability effects associated with disodium EDTA would have in fact been enhanced in the disodium EDTA test samples. In spite of this, the present Examples clearly demonstrate that disodium EDTA is preferred as a preservative agent/chelant over tetrasodium EDTA due to its ability to stabilize the active Peak 4 species, and to prevent aluminum salt aggregation/precipitation, thereby maintaining antiperspirant efficacy.

We claim:

1. An aqueous composition comprising an active antiperspirant ingredient and disodium EDTA,
    wherein the active antiperspirant ingredient comprises Aluminum Zirconium Tetrachlorohydrex-Glycine (ZAG), wherein the active antiperspirant ingredient is present in an amount of 0.5-6 weight % by total weight of the composition on an anhydrous basis,
    wherein the pH of the composition is from 2 to 5, and
    wherein the disodium EDTA is present in the composition in an amount of 0.1 weight % to 0.4 weight % by total weight of the composition.

2. The composition according to claim 1, exhibiting a Size Exclusion Chromatography (SEC) chromatogram having a SEC Peak 4 area:Peak 3 area ratio of at least 1.5.

3. The composition of claim 1, exhibiting a SEC chromatogram having a Peak 3 and/or Peak 5 area of less than 40% of a total area of Peaks 1, 2, 3, 4 and 5.

4. The composition according to claim 3, wherein the SEC chromatogram has no Peak 3 and/or Peak 5 area.

5. The composition according to claim 1, wherein the pH is 2.5 to 4.5.

6. The composition according to claim 5, wherein the pH is 3 to 4.

7. The composition according to claim 1, wherein the disodium EDTA is present in the composition in an amount of 0.2 weight % to 0.3 weight % by total weight of the composition.

8. The composition according to claim 1, wherein the composition is free of glycine other than glycine complexed with the active antiperspirant ingredient.

9. The composition according to claim 1, wherein the composition is free of calcium salts.

10. The composition according to claim 1, wherein the composition is free of tetrasodium EDTA.

11. The composition according to claim 1, further comprising one or more ingredients selected from: a deodorant active, an emollient, a surfactant, a gelling agent, a fragrance and an emulsifier.

\* \* \* \* \*

UNITED STATES PATENT AND TRADEMARK OFFICE
CERTIFICATE OF CORRECTION

PATENT NO. : 10,406,085 B2
APPLICATION NO. : 15/037383
DATED : September 10, 2019
INVENTOR(S) : Viktor Dubovoy et al.

Page 1 of 1

It is certified that error appears in the above-identified patent and that said Letters Patent is hereby corrected as shown below:

In the Specification

In Column 5, Line 37, after "0.4", delete "weight %," and insert -- weight % --, therefor.

In Column 7, Line 42, delete "stearate):" and insert -- stearate); --, therefor.

In Column 7, Line 52, delete "EO):" and insert -- EO); --, therefor.

In Column 8, Lines 14-15, delete "$(R^{10})_3SiO[(R^{11})_2SiO]_xSi(R^{12})(R^bO((C_2H_4O))_p(C_3H_6O)_s(R^c)O]^ySi(R^{13})$" and insert -- $(R^{10})_3SiO[(R^{11})_2SiO]_xSi(R^{12})(R^bO(C_2H_4O)_p(C_3H_6O)_s(R^c)O]^ySi(R^{13})_3$ --, therefor.

In Column 8, Line 25, delete "$-((C_2H_4O)_p-$" and insert -- $-(C_2H_4O)_p-$ --, therefor.

In Column 8, Line 44, delete "R" and insert -- $R^c$ --, therefor.

In Column 8, Lines 51-52, delete "$-R^b-O-(C_2H_4O)-R^c.$" and insert -- $-R^b-O-(C_2H_4O)_p-R^c.$ --, therefor.

In Column 8, Line 67, delete "ABIL3" and insert -- ABIL --, therefor.

In Column 15, Line 11, after "(0.4 weight %", delete "ACH:" and insert -- ACH; --, therefor.

In Column 16, Line 5, delete "ZAG/i" and insert -- ZAG/1 --, therefor.

Signed and Sealed this
Tenth Day of December, 2019

Andrei Iancu
*Director of the United States Patent and Trademark Office*